United States Patent
Miyazaki et al.

(10) Patent No.: US 7,636,416 B2
(45) Date of Patent: Dec. 22, 2009

(54) X-RAY CT APPARATUS COMPRISING A TUBE CURRENT CONTROL UNIT

(75) Inventors: Osamu Miyazaki, Moriya (JP); Koichi Hirokawa, Kashiwa (JP); Toshiyuki Irie, Hitachi (JP)

(73) Assignee: Hitachi Medical Corporation, Tokyo (JP)

( * ) Notice: Subject to any disclaimer, the term of this patent is extended or adjusted under 35 U.S.C. 154(b) by 153 days.

(21) Appl. No.: 11/884,099

(22) PCT Filed: Feb. 27, 2006

(86) PCT No.: PCT/JP2006/003624

§ 371 (c)(1),
(2), (4) Date: Aug. 8, 2007

(87) PCT Pub. No.: WO2006/090877

PCT Pub. Date: Aug. 31, 2006

(65) Prior Publication Data

US 2008/0107231 A1 May 8, 2008

(30) Foreign Application Priority Data

Feb. 25, 2005 (JP) .............................. 2005-051497

(51) Int. Cl.
H05G 1/34 (2006.01)
(52) U.S. Cl. .......................... 378/16; 378/108; 378/109; 378/110
(58) Field of Classification Search ............ 378/16, 378/95, 108, 109, 110
See application file for complete search history.

(56) References Cited

U.S. PATENT DOCUMENTS

| 5,379,333 | A | * | 1/1995 | Toth | 378/16 |
| 5,400,378 | A | * | 3/1995 | Toth | 378/16 |
| 5,822,393 | A | * | 10/1998 | Popescu | 378/108 |
| 5,867,555 | A | * | 2/1999 | Popescu et al. | 378/16 |
| 6,385,280 | B1 | * | 5/2002 | Bittl et al. | 378/16 |
| 6,490,337 | B1 | | 12/2002 | Nagaoka et al. | |
| 6,754,301 | B2 | * | 6/2004 | Horiuchi | 378/16 |
| 6,775,352 | B2 | * | 8/2004 | Toth et al. | 378/108 |
| 6,901,129 | B2 | * | 5/2005 | Tachizaki et al. | 378/4 |
| 6,954,513 | B2 | * | 10/2005 | Horiuchi | 378/4 |
| 6,987,828 | B2 | * | 1/2006 | Horiuchi | 378/16 |
| 6,990,172 | B2 | * | 1/2006 | Toth et al. | 378/16 |
| 7,031,423 | B2 | * | 4/2006 | Tsukagoshi | 378/4 |
| 7,072,437 | B2 | * | 7/2006 | Seto | 378/20 |
| 7,103,139 | B2 | * | 9/2006 | Nagaoka et al. | 378/16 |
| 7,106,824 | B2 | * | 9/2006 | Kazama et al. | 378/16 |
| 7,142,630 | B2 | * | 11/2006 | Suzuki | 378/16 |
| 7,203,270 | B2 | * | 4/2007 | Okumura et al. | 378/16 |
| 7,215,733 | B2 | * | 5/2007 | Nabatame | 378/16 |
| 2004/0086076 | A1 | | 5/2004 | Nagaoka et al. | |

FOREIGN PATENT DOCUMENTS

| JP | 8-166995 | 6/1996 |
| JP | 2001-276040 | 10/2001 |
| JP | 2002-263097 | 9/2002 |

* cited by examiner

*Primary Examiner*—Allen C. Ho
(74) *Attorney, Agent, or Firm*—Cooper & Dunham, LLP

(57) ABSTRACT

An X-ray CT apparatus includes a projection data analysis part that reconstructs a tomographic image at an imaging portion of the object used for analysis from the projection data and produces a control profile by reprojecting the reconstructed tomographic image, and a tube current control part that controls value of current to be fed to the X-ray tube based on the produced control profile.

11 Claims, 6 Drawing Sheets

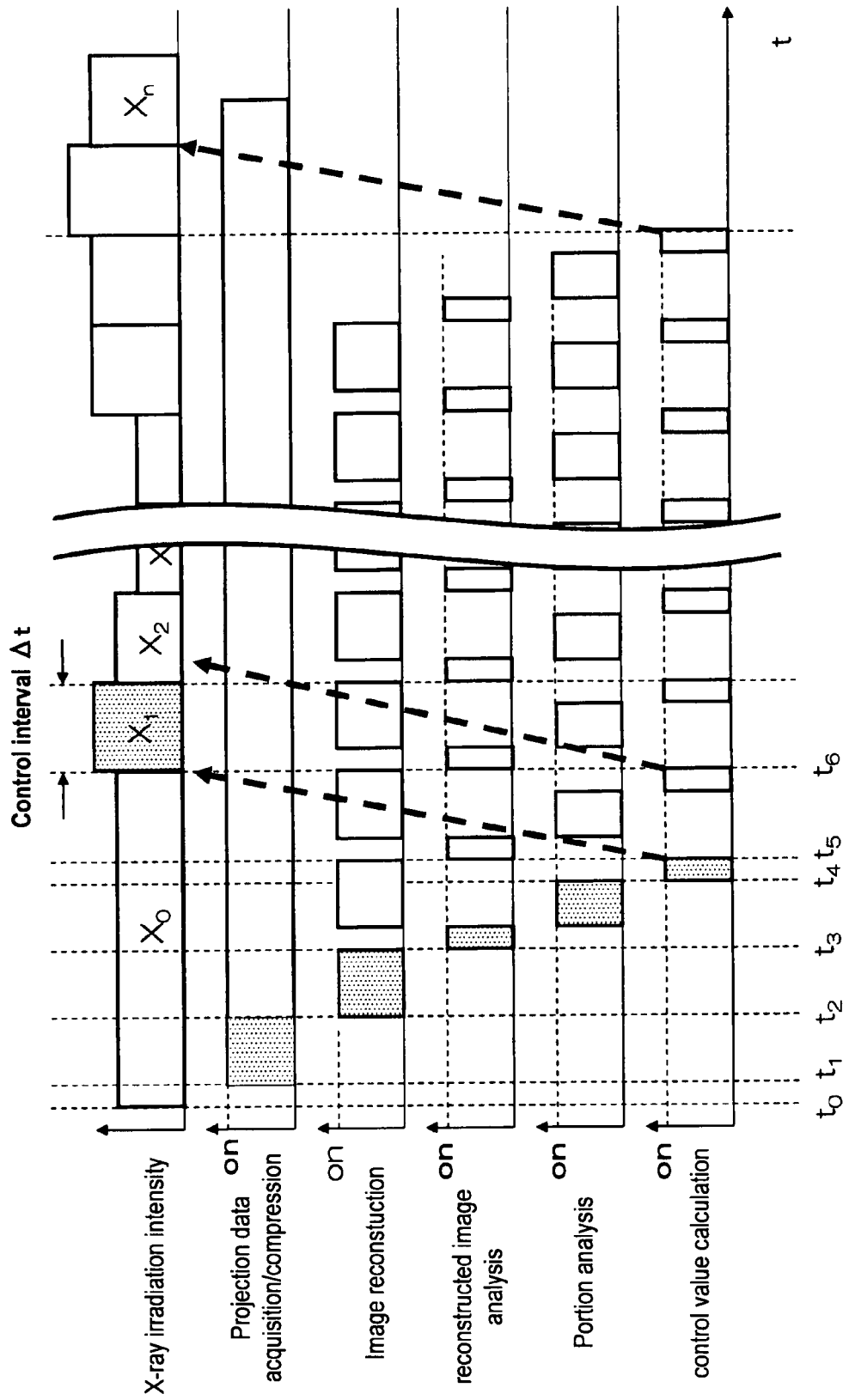

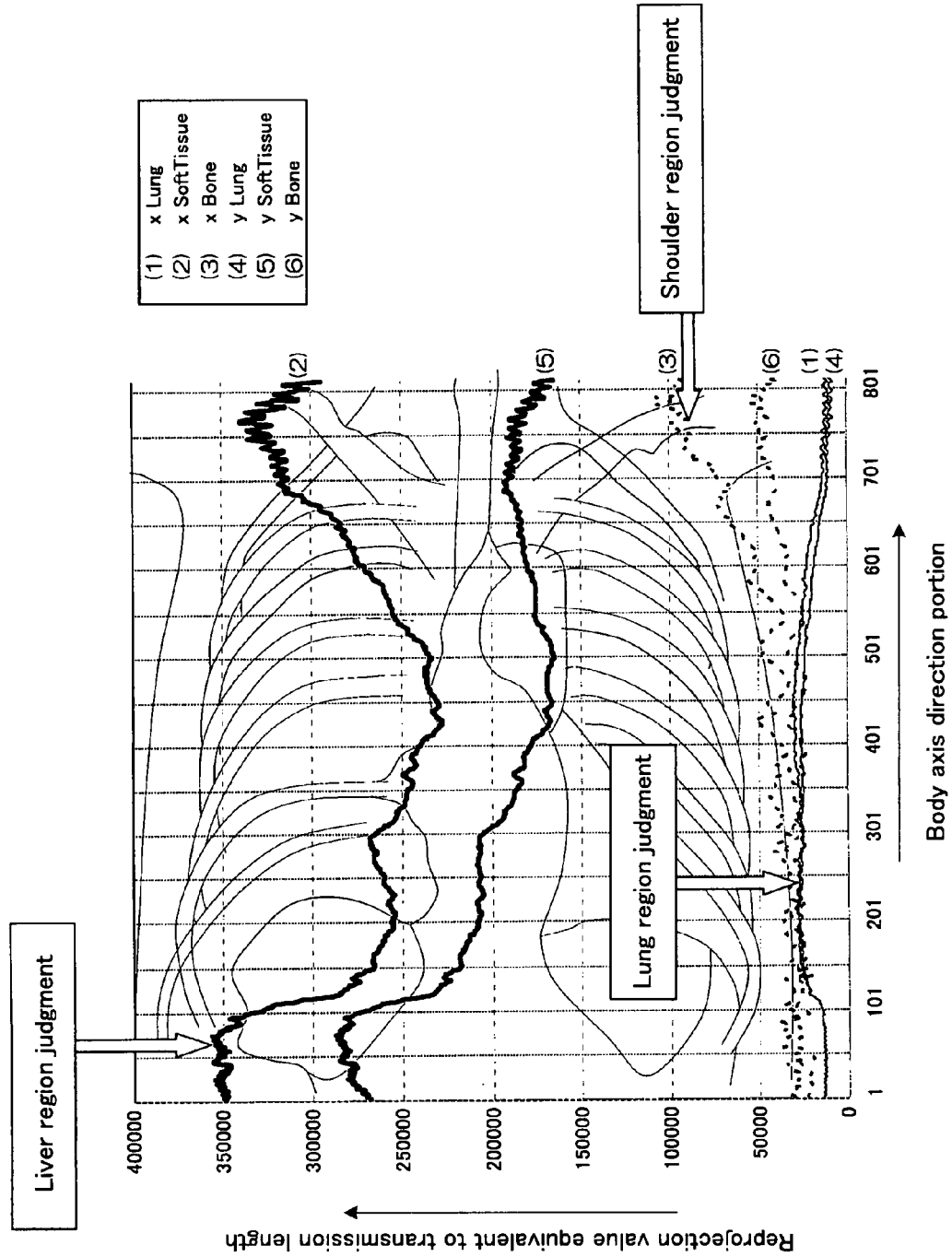

X-RAY CT APPARATUS COMPRISING A TUBE CURRENT CONTROL UNIT

TECHNICAL FIELD

The present invention relates to an improvement in an X-ray CT apparatus that permits to control X-ray source current (herein after will be called as X-ray tube current) fed to an X-ray source (herein after will be called as X-ray tube) which determines X-ray irradiation density to an imaging region of an object to be examined depending on positions in body axial direction of the object.

The present application is an application claiming Paris Convention priority based on Japanese Patent Application No. 2005-051497 under Japanese Patent Law and is an application, which enjoys the benefit of Japanese Patent Application No. 2005-051497 by reference.

CONVENTIONAL ART

Quality of images obtained by an X-ray CT apparatus is determined by factors such as spatial resolution and noises contained in the images. Among these factors, the image noises primarily depend on the intensity of transmitting X-rays. The intensity of transmitting X-rays is determined by the intensity of irradiating X-rays and X-ray transmission length across the cross section of an imaging portion of an object. The intensity of irradiating X-rays is determined by a current fed to an X-ray tube. An absorption of the cross section of the imaging portion of the object is determined, when assuming configuration of a human body as an ellipse, depending on difference of the transmission length between front face-back face direction (herein after may be called as front and rear direction) thereof and side face to side face direction (herein after may be called as right to left direction). A reduction of transmitting X-ray intensity increases noise rate with respect to transmitting X-ray intensity signals.

Technology for improving the reduction of transmitting X-ray intensity is, for example, disclosed in patent document 1. In the patent document 1, the improvement for the reduction of the transmitting X-ray intensity is achieved by the following steps. At first, scanogram image data which are taken prior to measurement of tomographic images (also called as real scanning) used for diagnosis are analyzed and with the analyzed scanogram image data, a three dimensional like transmission length model of a object is prepared. Subsequently, a variation pattern of X-ray tube current depending on an imaging portion of the object is set based on the previously prepared three dimensional like transmission length model and scanning conditions in the real scanning.

Patent document 1: JP-A-2002-263097

However, the conventional art is confined to the setting of the X-ray tube current control values based on the prepared scanogram and does not take in to account a fact that X-ray absorption amount in scanogram differs depending on respective tissues of the object such as bones where X-ray attenuation is large and soft tissues. For example, at a portion such as a shoulder having many bones, the transmission X-ray intensity shorts. In the case of such shorting of the transmission X-ray intensity, the amount of noises with respect to the transmission X-ray intensity signals increases. Namely, even if the conventional art is employed, a problem still remains unsolved that the quality of tomographic images reduces at portions of a object containing many bones because of the noise amount increase due to shortage of the transmission X-ray intensity.

BRIEF SUMMARY

In an aspect of this disclosure, there is provided an X-ray CT apparatus configured to obtain tomographic images of high quality even at portions of a object where variation of transmission X-ray intensity is large.

In an aspect of this disclosure, there is provided an X-ray CT apparatus comprising an X-ray source irradiating X-rays to an object, an X-ray detector that is disposed oppositely to the X-ray source in a manner placing the object therebetween and is to detect transmitting X-rays through the object as projection data, a rotating means that rotates the X-ray source and the X-ray detector, a control means that collects the projection data from plural angular directions obtained through rotation of the X-ray tube and the X-ray detector by the rotating means, performs reconstruction computation of these collected projection data to produce tomographic images or the object as well as controls the X-ray source and the rotating means and a display means that displays the produced tomographic images, characterized in that the X-ray CT apparatus further comprising a projection data analysis means that reconstructs a tomographic image at an imaging portion of the object used for analysis from the projection data and produces a control profile by reprojecting the reconstructed tomographic image and a tube current control means that controls value of current to be fed to the X-ray tube based on the produced control profile.

According to the present invention, tomographic images of high quality can be obtained even at portions of an object where variation of transmission X-ray intensity is large.

BRIEF DESCRIPTION OF THE DRAWINGS

FIG. 4 (B) is an image of the reconstructed tomographic image used for analysis after being objected to a threshold processing and a diagram for explaining an attenuation profile B by bones in X direction obtained by reprojecting the image in X direction.

FIG. 5 (B) is an image of the reconstructed tomographic image used for analysis after being objected to a threshold processing and a diagram for explaining an attenuation profile B by bones in X direction obtained by reprojecting the image in X direction.

FIG. 6 is a timing chart for explaining respective processes performed by the projection data analysis device according to the present invention as shown in FIG. 2, when a real scanning is started with the X-ray CT apparatus according to the present invention.

FIG. 7 is a model diagram showing a reprojected result in X direction and Y direction obtained along the body axis direction of a object with regard to three respective tissues of soft tissue, bones and lung field from a reconstructed image of the object used for analysis obtained by a projection data analysis device together with a scanogram of the corresponding portions of the object.

BEST MODE FOR CARRYING OUT THE INVENTION

Figure 1:
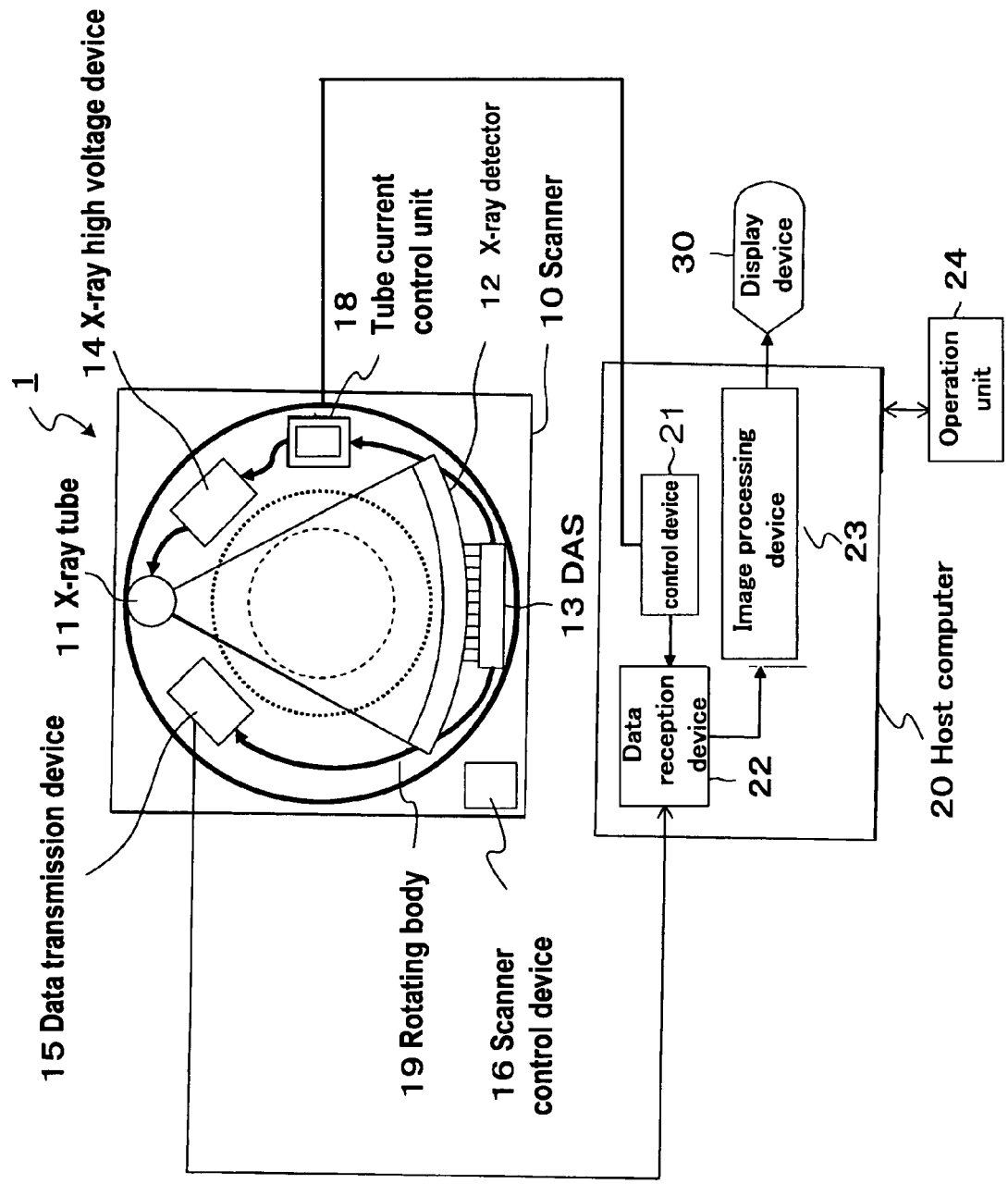
FIG. 1 is a schematic constitutional diagram of an X-ray CT apparatus to which the present invention is applied.

Herein below, an embodiment of an X-ray CT apparatus according to the present invention will be explained with reference to the accompanied drawings. An X-ray CT apparatus 1 according to the present embodiment measures projection data of a object while controlling X-ray tube current depending on an X-ray tube position (θ, Z). Further, in all of the drawings for explaining the embodiment of the present invention, ones having the same functions are designated with the same reference numerals and repetitive explanation thereof is omitted.

FIG. 1 shows a constitution of the X-ray CT apparatus 1 according to the present embodiment. The X-ray CT apparatus 1 is constituted by a scanner 10, a host computer 20 connected to the scanner 10, an operation unit 24 connected to the host computer 20 and a display unit 30.

At first the constitutional elements of the scanner 10 will be explained.

An X-ray tube 11 irradiates X-rays to an object. An X-ray detector 12 is disposed oppositely to the X-ray tube 11 and detects X-rays transmitted through the object. A data measurement device (DAS (Data Acquisition System)) 13 performs a predetermined data processing to the transmitted X-rays detected by the X-ray detector 12 and calculates projection data. An X-ray high voltage device 14 is a power source feeding for the X-ray tube 11 and of which voltage, current and power supply time (corresponding to an X-ray irradiation time) is designed to be able to set by the operation unit 24 which will be explained later. A voltage applied from the power source is called as tube voltage and a current therefrom is called as a tube current. A data transmission device 15 transfers data between a rotation system—a stationary system and includes a slip ring and brushes or a rotary transformer. A scanner control device 16 controls amount of rotation of rotary plate (a scanner) to which the X-ray tube 11 and the X-ray detector 12 are attached. A projection data analysis device 17 reconstructs tomographic images of the object from the projection data calculated by the data measurement device 13. A tube current control unit 18 controls the tube current of the X-ray tube 11. These respective constitutional elements are carried on a rotary body rotatable around the object.

Now, the host computer 20 performs overall control on the X-ray CT apparatus 1 and includes the following constitutional elements. A control device 21 is constituted by such as a CPU and a memory for performing the overall control on the X-ray CT apparatus 1. A data reception device 22 receives measurement data from the transmission device 15 in the scanner 10. An image processing device 23 performs image reconstruction computation based on the measurement data received by the data reception device 22 to produce the tomographic images. The operation unit 24 is such as a track ball, a mouse and a keyboard for providing such as an input command with regard to ON/OFF of a tube current control mode.

Further, the display device 30 is provided with a function of displaying produced tomographic images. Although the illustration is omitted, the X-ray CT apparatus 1 is provided with a patient table for laying the object during the scanning. In the X-ray CT apparatus 1 according to the present embodiment, ON/OFF of the tube current control mode can be performed by the input command from the operation unit 24. During the tube current control mode OFF, the real scanning is performed with a constant irradiation X-ray intensity. The data of transmitted X-ray intensity measured by the X-ray detector 12 are, after being converted into digital data by the DAS 13, transferred from the data transmission device 15 in the rotary system to the stationary system. In the stationary system, the projection data are acquired by a reception unit in the data reception device 22, send to the image processing device 23 and, after being reconstructed as tomographic images, the images are displayed on the display device 30 for image interpretation.

The constitution of the projection data analysis device 17 according to the first embodiment will be explained based on FIG. 2.

The projection data analysis device 17 determines a control value for the tube current to be flown to the X-ray tube 11. The projection data analysis device 17 includes an analysis use image reconstruction unit 17a, a reconstructed image analysis unit 17b and a tube current control value calculation unit 17c. The analysis use image reconstruction unit 17a, when projection data are inputted, starts the reconstruction processing of the projection data and calculates a tomographic image for every predetermined view interval. The reconstructed image analysis unit 17b analyzes the reconstructed images and calculates respective maximum reprojection values at, for example, bones and soft tissue of the cross section, the maximum reconstruction value obtained by totaling these and converted transmission lengths including longitudinal and lateral width of the images. The tube current control value calculation unit 17c calculates an optimum tube current control value depending on the obtained converted transmission lengths and inputs imaging conditions including new tube current value to the X-ray high voltage device 14.

Further, The projection data analysis device 17 can be provided with a portion weight determination means 17d.

Figure 2:
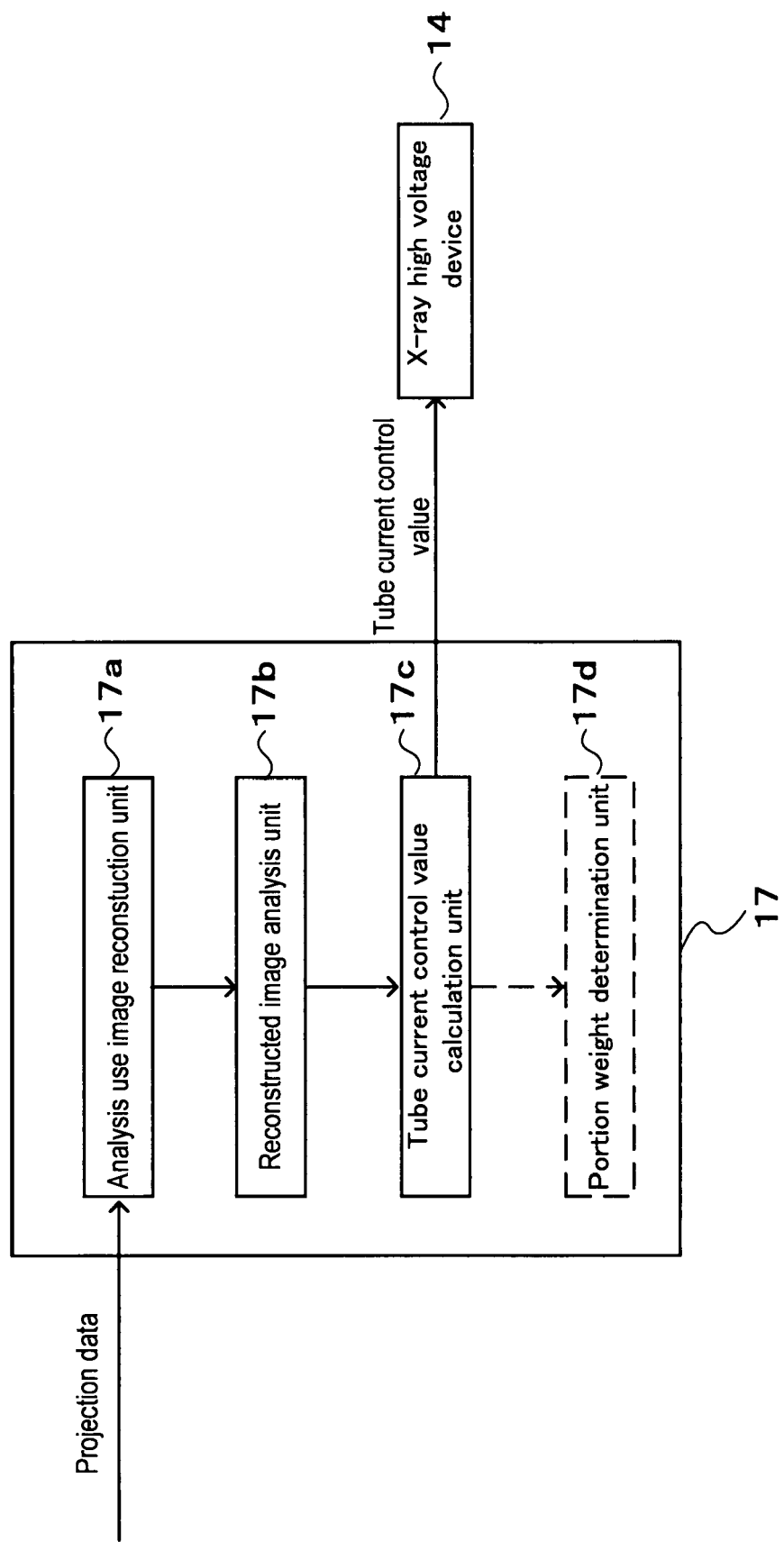
FIG. 2 is a block diagram for explaining a first embodiment of a projection data analysis device, which is applied for a tube current control unit in the present invention.

More specifically, as shown by a dotted portion in FIG. 2, the portion weight determination unit 17d can be added. Information about organ portions is obtained by evaluating an absolute amount, ratio or variation of the reprojection value. The portion weight determination unit 17d modifies the current control value obtained by the current control value calculation unit 17c for every organ portions by making use of the obtained organ portion information and outputs a new current control value to the X-ray high voltage device 14. For example, while weight coefficients are determined beforehand for every organ portions, and a new current control value is determined by multiplying a weight with the calculated current value. For example, when the object is a female, the weight is set to a small value for a pelvic cavity (hypogastrium) and the amount of irradiation is controlled lower than that obtained from the transmission length.

In the tube current control unit 18 in the X-ray CT apparatus 1, the tube current is controlled in the following steps. At first, during a real scanning an analysis use tomographic image is at any time reconstructed from the projection data measured (measurement data). The analysis use tomographic image reconstructed at any time is analyzed and a new tube current value is determined according to the analysis. The newly determined tube current value is directly fed back to the X-ray tube 11. In the series of these processing flow, after imaging a scanogram and determining an imaging range and original values of X-ray condition, the process moves to a real scanning to start projection data measurement for every view (view data measurement). The X-ray conditions including the tube current value are renewed at any time during the real scanning.

Figure 3:
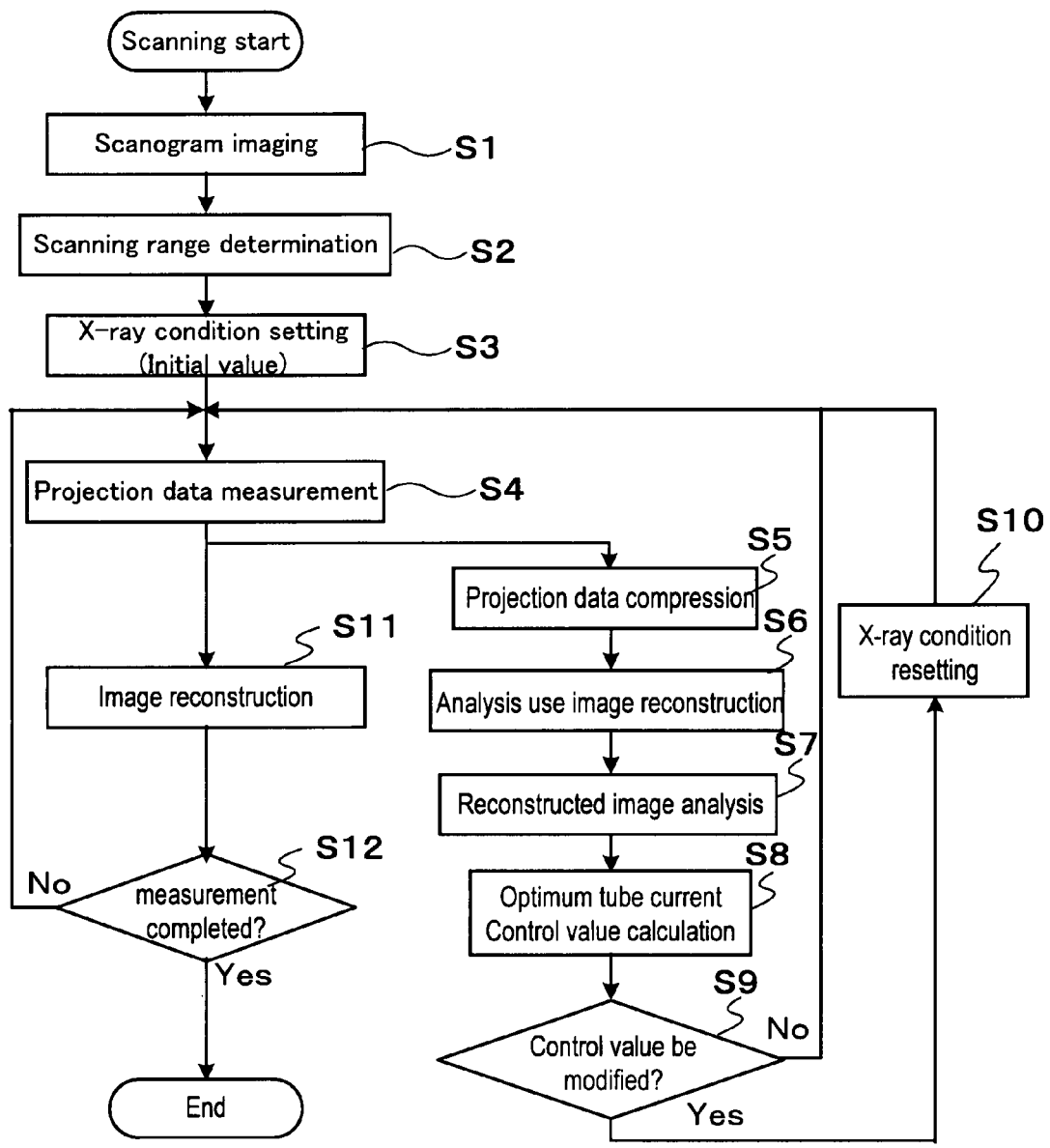
FIG. 3 is a flowchart for explaining a control processing flow of tube current applied in the present invention.

Herein below, the flow of tube current control processing will be explained in detail based on FIG. 3

At first, in step S1, a scanogram imaging is performed with the X-ray CT apparatus 1. In step S2, based on the scanogram image taken in step S1 the imaging range is set. In step S3, conditions for X-ray imaging including the tube current value are set. The tube current value set herein is the original value for the imaging condition. In step S4, the view data measurement is performed according to the imaging range and the imaging conditions set at steps S2 and S3.

In step S5, by means of a data compression device provided at the input stage in the projection data analysis device 17, compression processing of the projection data is performed.

In step S6, the projection data compressed in step S5 are input to the analysis use image reconstruction means 17a in the projection data analysis device 17. The analysis use image reconstruction means 17a performs a reconstruction processing for the image used for analysis. In step S7, based on the analysis use image prepared in step S6, the reconstructed image analysis means 17b analyzes the reconstructed image and calculates a converted transmission length in the analysis use image according to a predetermined reference material (for example, water). In step S8, the tube current control value calculation means 17c calculates an optimum tube current value based on the obtained converted transmission length and by making use of such as a transmission length-control value conversion table. In step S9, based on the optimum tube current value calculated by the tube current control value calculation means 17c whether or not the tube current value for the X-ray high voltage device 14 is to be modified is judged based on the deviation from the original conditions. When the tube current is not modified, the process returns to step S4 and the view data measurement is continued based on the instant tube current value. When the tube current value is modified, the process advances to step S10, the X-ray conditions including the tube current are reset and the new reset tube current value is input to the X-ray high voltage device 14. Then the process returns to step S4 and the view data measurement is performed according to X-ray conditions with the new current control value.

In step S11, based on the projection data measured at step S4, the image processing device 23 performs the image reconstruction processing. The step S11 and the steps S5~S10 can be performed in parallel. Through this parallel processing a speed of the series of measurement and data processing can be increased. The projection data obtained in step S4 are output through the data transfer device 15 in the rotary system to the host computer 20. In step S11, the data transfer device 22 in the host computer 20 receives the projection data and outputs the same to the image processing device 23. The image processing device 23 performs the image reconstruction processing based on the projection data and outputs a tomographic image to the display device 30. In step S12, whether the measurement is completed or not is judged and when the answer is "Yes", the measurement ends. When the answer is "No", the process returns to step S4.

Now, the reconstruction image analysis means 17b will be explained in further detail. The reconstruction image analysis means 17b is primarily for performing the reprojection processing of the analysis use reconstruction image and can calculate the converted transmission length information in the reprojection direction. Further, the reconstruction image analysis means 17b according to the present embodiment can perform a threshold processing at the time of reprojecting. For example, reprojection data B of bones as shown in FIGS. 4 and 5 can be calculated.

Figure 4:
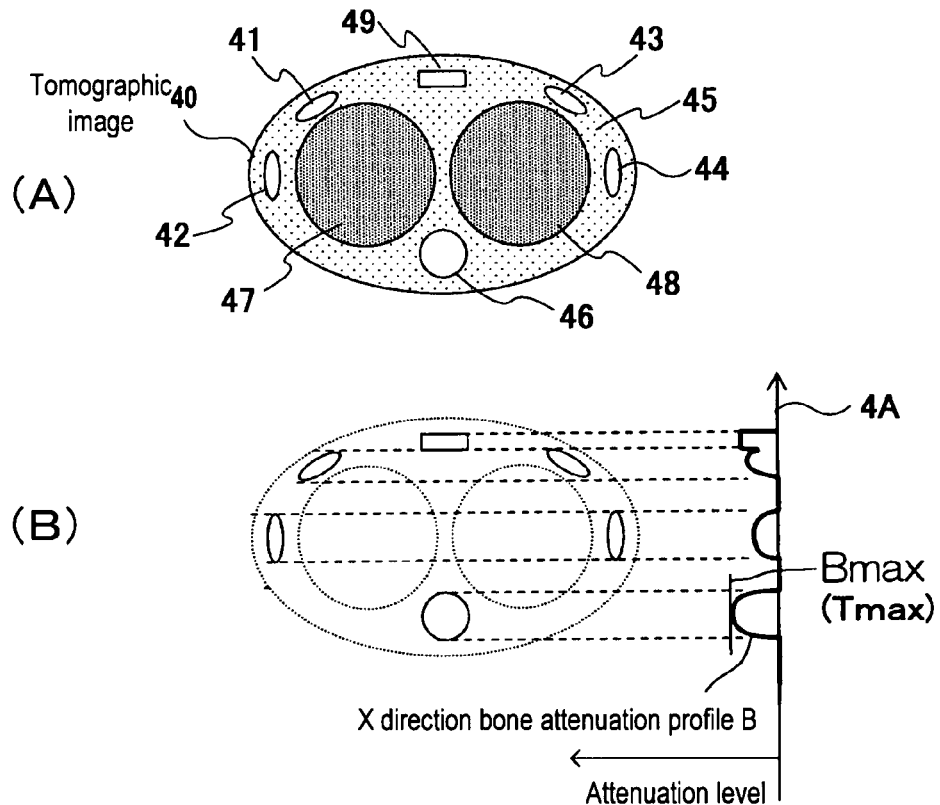
FIG. 4 (A) is a reconstructed tomographic image used for analysis that is reconstructed based on projection data of an imaging portion of a object having a comparatively less bones by the projection data analysis device according to the present invention as shown in FIG. 2.

FIG. 4 (A) shows an example of a tomographic image 40 containing bone portions (B) 41, 42, 43, 44, 46 and 49 and soft tissues (T) 45, 48 and 47. In FIG. 4 (A), the tomographic image 40 is objected to a threshold processing with a predetermined CT value and a variety of regions such as bones and soft tissues are extracted. Then, an X-ray attenuation profile of region extracted tomographic image 40 from X direction is calculated as 4A. Among the calculated profile the maximum reprojection value Bmax is determined. In the same manner the maximum reprojection values Bmax other than the X direction are determined and all of the values around the object are added to thereby obtain a control profile, which is reflected to the X-ray tube current.

Figure 5:
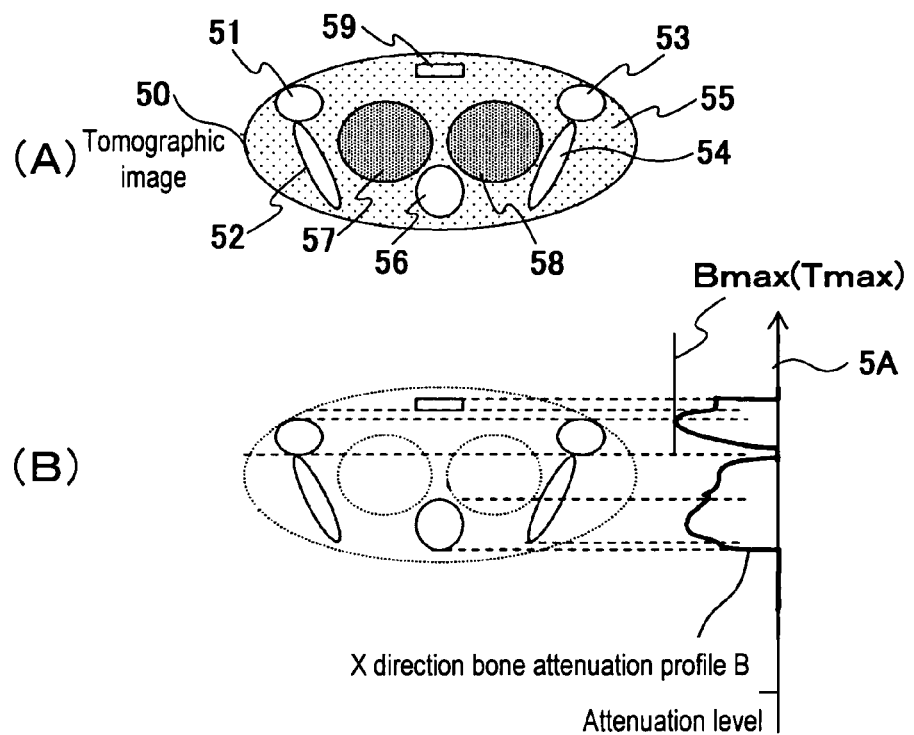
FIG. 5 (A) is a reconstructed tomographic image used for analysis that is reconstructed based on projection data of an imaging portion of a object having many bones by the projection data analysis device according to the present invention as shown in FIG. 2.

FIG. 5 is an example wherein a converted transmission length at another portion than that in FIG. 4 is obtained. Like in FIG. 4, an example of a tomographic image 50 containing bone portions (B) 51, 52, 53, 54, 56 and 59 and soft tissues (T) 55, 58 and 57 is shown. In this example an X-ray attenuation profile is calculated as 5A. As will be understand when comparing 4A in FIG. 4 with 5A in FIG. 5, the maximum reprojection values Bmax vary largely depending on the measurement positions of the object.

The tube current control value calculation means 17c converts the obtained control profile to a converted transmission length and calculates an optimum tube current control value from the converted transmission length. When calculating the tube current control value, the object is approximated to an ellipse filled with a uniform material (for example, water) and the conversion is performed by using an equivalent transmission length of the material (for example, water) having an ellipse approximated configuration as the reference. For example, since $\Sigma F(j)$ is an integrated value of entire CT values in reprojection direction (for example, X direction), a water equivalent transmission length Dw[mm] is determined with the following formula (1). Wherein CT value of air is assumed as 0 and water as 1000.

$$Dw = \Sigma F(j)*p/N*1000 \tag{1}$$

Herein, p is a pixel size {mm} and N is a number of reprojection beams, which covers the object (corresponding to a width of the object when viewed from the reprojection direction). Current control values Q for the tube current are provided beforehand as a function of Dw (alternatively, in a form of a table) and are determined according to formula (2). Since as the analysis object reconstructed images are used instead of the projection data, an evaluation accuracy of cross sections of the object is enhanced.

$$Q = f(Dw) \tag{2}$$

When the reprojection processing with threshold value is performed, the transmission lengths of soft tissue and bones further can be calculated according to formulae (3) and (4). Wherein Nt and Nb are numbers of reprojection beams containing respectively soft tissue and bones, and the CT value of bones is assumed as 2000 and CT value of soft tissue as 1040.

$$Db = \Sigma F(j)*p/N*2000 \tag{3}$$

$$Dt = \Sigma F(j)*p/N*1040 \tag{4}$$

The current control value is determined according to formula (2) after determining water transmission length while weighting respectively the transmission lengths of the tissues and bones according to formula (5).

Although weight coefficients Wt and Wb can be assumed as 1.0 in common, however, since when the tube voltage is low, an influence of bones increases, an adjustment is possible to set the tube current at comparatively high by increasing the bone weight Wb large.

Further, in the case of an infant, since the influence of bones is small, it is preferable to set the tube current as low as possible so as to suppress X-ray exposure. In such instance, the weight of bones Wb can be adjusted low.

Further, as weights for every portions of imaging organs, Wt and Wb can be used.

$$Dw=Wt*Dt+Wb*Dt \quad (5)$$

Further, in a method of not using the weight coefficients, a relationship between transmission length of soft tissue and transmission length of bones and optimum tube current values are determined beforehand. In such instance, the current control value Q for the optimum tube current is expressed as formula (6).

$$Q=f(Dt,Db) \quad (6)$$

In such instance, while analyzing clinical data likely, a two dimensional table can be determined statistically.

In any events, since a cross section of a object of which the transmission length of bones is taken into account can be calculated, measurement accuracy of a cross section of the object is further enhanced.

The reprojection processing can be performed on one sheet of analysis use reconstruction image in plural directions and when the processing is performed in more than one directions, in that X direction (3 o'clock direction) and Y direction (0 o'clock direction), the transmission length at the advanced phase in 6 o'clock and 9 o'clock directions can be estimated. When controlling the tube current in a sinusoidal wave or in any function, it is sufficient if the maximum value and the minimum value thereof are given, an alternate computation in X direction and Y direction can be performed in order to reduce computation amount.

Now, an operation of the X-ray CT apparatus 1 will be explained. When the X-ray detector 12 in the X-ray CT apparatus 1 according to the present embodiment includes, for example, detector elements for 1024 channels, view data are captured 1024 time for every one rotation. Further, with regard to the projection data from the DAS 13, an average value of center two rows in the multi-slice detector is constituted to be inputted to the projection data analysis device 17 through a data compression device provided at the input stage in the projection data analysis device 17. Further, by bundling every 8 sample data both in view direction and channel direction, view data of 128 channels are inputted 128 times for every one revolution. When assuming that sampling interval of the original data is 0.5 mm, an analysis use image having a resolution of about 4 mm can be reconstructed. Further, when assuming that the matrix of the analysis use reconstructed image is 128 pixels, the maximum FOV (region of interest) will be 512 mm at resolution of 4 mm. When comparing with a reading use reconstructed image, since the reconstructed matrix is 1/16 and the number of views is 1/8, computation scale thereof will become about 1/128. In this instance, a correction processing with filter is performed by means of a blurring correction filter, which is stored in advance by performing Fourier transformation at 256 points. Further, a reverse projection processing is performed after application of the blurring correction filter. When completing the reverse projection processing of the view data necessary for the reconstruction, the analysis use tomographic image is reconstructed. In addition, although it is necessary to hold data of air and offset data together with data of water, since the amount of such as the data of air and the offset data is sufficient those for one view, the small memory capacity required for the respective data is sufficient.

In the case of multi-slice CT, when the number of rows to be arranged increases, a three dimensional back projection computation such as using Feldkamp method is necessary, however, according to the present embodiment, even if only specific rows are reconstructed as they are with a conventional two dimensional reconstruction method, the results show a sufficient practicality.

Further, the estimation accuracy of the converted transmission length of the cross section for evaluation can be enhanced, if, in addition to the reconstruction only of the images at the rows near the center, images at the edge rows are reconstructed together and the converted transmission lengths in the body axis direction are obtained at plural points.

Prior to the real scanning, an initial value X0 of X-ray condition and time interval $\Delta t$ for control command are inputted. The X0 can be an optimum value obtained from an analysis result of the scanogram or value determined empirically by an operator.

Further, although the time interval $\Delta t$ for control command can be determined arbitrary, however, if the tube current value is renewed so frequently and the X-ray exposure is not optimized, the command renewal is meaningless, therefore, the time interval is determined in view of such as the response time of the control system and, of course, the time interval can be defined by such as the number of views and an angular interval. For example, when assuming that the number of views for one rotation is 128 and the tube current value is outputted for every 32 views, the command can be renewed four times for every one rotation.

FIG. 6 shows a timing chart of the respective processes during scanning. When the scanning is started at t0 and X-ray exposure is started, in synchronism thereto a data collection operation is started. Herein the initial value of the tube current is assumed as X0. All of the measured data are sent to the data transfer device 15 and are transferred to the stationary system. The data captured in the host computer 20 are reconstructed in the image processing device 23 as a reading use tomographic image.

On the other hand, the projection data analysis device 17 performs the analysis use image reconstruction, the reconstructed image analysis and the optimum tube current control value calculation processing so as to determine a tube current control value. The analysis use image reconstruction, the reconstructed image analysis and the optimum tube current control value calculation processing are performed respectively in a pipeline manner. A new tube current control value obtained through the optimum tube current control value calculation processing is sent to the X-ray high voltage device 14 and the feedback is for the first time effective at t6. The timing when the feedback becomes effective can be used as a substantial imaging start point.

The tube current value obtained here is what was set based on an analysis use image reconstructed from the projection data obtained around time t1-t2 and contains corresponding phase (angular) information. Herein, the X-ray high voltage device 14 alters the actual control value at the corresponding phase t6.

In the case of determining the tube current control value by directly processing the projection data as in the conventional art, when such as a preamplifier gain, log conversion gain and distance between focal point-detector vary, parameters for the tube current had to be reviewed, however, in the present embodiment, since the tube current control value is set based on the CT value representing an absolute value, a stable control can be achieved.

FIG. 7 shows reprojection results in X and Y directions of respective three tissues of soft tissue, bones and lung field. The horizontal axis represents body axis direction and corresponds to the positions of the scanogram shown in the background. Herein, when noting to the reprojection result of the soft tissue, only the lung field existing position shows a high reprojection value in both X and Y directions.

On the other hand, the reprojection value of the bones increases near the shoulder. In this manner, it is understood that the results show the respective features of the imaged portions. Thereby, according to the present embodiment, respective portions can be judged by making use of the respective reprojection values.

In the present embodiment, although exposure doses are constituted to be automatically controllable for every portion, through setting a portion particularly desired to be lowered of the exposure doses by an operator using such as a scanogram, control of the exposure doses can be preformed by making use of such information, however, when the tube current value is set so as to follow according to the measurement portions of the tomographic image, such is further desirable in view of its user friendliness.

Further, in the present embodiment, an example where the transmission length is converted into X-ray absorption coefficient of water was explained, however, the material used as a parameter of the X-ray absorption coefficient is not limited to water, but any material such as bone and soft tissue can be selected. Because it is sufficient if a object can be converted in a form of a transmission length of a predetermined material.

The invention claimed is:

1. An X-ray CT apparatus comprising:
    an X-ray tube irradiating X-rays to an object,
    an X-ray detector that is disposed oppositely to the X-ray tube in a manner placing the object therebetween and is to detect transmitted X-rays through the object as projection data,
    a rotating means that rotates the X-ray tube and the X-ray detector,
    a control means that collects the projection data from plural angular directions obtained through rotation of the X-ray tube and the X-ray detector by the rotating means, performs reconstruction computation of these collected projection data to produce tomographic images of the object as well as controls the X-ray tube and the rotating means,
    a display means that displays the produced tomographic images,
    a projection data analysis means that reconstructs a tomographic image at an imaging portion of the object used for analysis from the projection data and produces a control profile by reprojecting the reconstructed tomographic image during real scanning, and
    a tube current control means that modifies or renews, during said real scanning and based on the control profile produced by the projection data analysis means, a value of current to be fed back to the X-ray tube.

2. An X-ray CT apparatus according to claim 1, characterized in that the projection data analysis means, when X-rays are irradiated from a predetermined direction, produces the control profile based on an X ray attenuation profile of regions in the predetermined direction.

3. An X-ray CT apparatus according to claim 2, characterized in that the projection data analysis means determines a maximum value among an X-ray attenuation profile on a predetermined direction and produces the control profile by adding all of the maximum value around the object.

4. An X-ray CT apparatus according to claim 1, characterized in that the projection data analysis means comprises:
    an analysis use image reconstruction means which reconstructs an analysis use tomographic image from a part of the projection data,
    a reconstructed image analysis means which calculates an X-ray transmission length of a reference material having a predetermined X-ray absorption as a converted transmission length with regard to the reconstructed analysis use tomographic image and
    a tube current control value calculation means which calculates an amount of current to be fed to the X-ray tube based on the calculated converted transmission length.

5. An X-ray CT apparatus according to claim 4, characterized in that the projection data analysis means further comprises a portion weight determining means which modifies the current control value calculated by the tube current control value calculation means by making use of organ portion information for every organ portions.

6. An X-ray CT apparatus according to claim 4, characterized in that the projection data analysis means takes a scanogram image of the object, sets initial conditions for X-ray imaging including an imaging range and a tube current value based on the scanogram image, measures the projection data according to these set imaging range and the imaging condition, performs the reconstruction processing of the analysis use image by making use of the measured projection data, produces the control profile from a predetermined direction of the analysis use image objected to the reconstruction processing, determines the converted transmission length based on the produced control profile and calculates the tube current value from the determined converted transmission length.

7. An X-ray CT apparatus according to claim 6, characterized in that the projection data analysis means calculates the tube current value from the converted transmission length by making use of the reference material.

8. An X-ray CT apparatus according to claim 6, characterized in that the projection data analysis means provides predetermined weights to a bone transmission length and a soft tissue transmission length and calculates the converted transmission length.

9. An X-ray CT apparatus according to claim 8, characterized in that the predetermined weighting is performed, after specifying an organ portion of the object based on the analysis use tomographic image, according to the specified organ portion.

10. An X-ray CT apparatus according to claim 6, characterized in that the converted transmission length to be analyzed is converted by transmission lengths including water equivalent transmission length, bone transmission length and soft tissue transmission length.

11. An X-ray CT apparatus comprising:
    an X-ray tube configured to irradiate X-rays to an object;
    an X-ray detector disposed on an opposite side of the object relative to the X-ray tube and configured to detect transmitted X-rays that passed through the object as projection data;
    a rotating part configured to rotate the X-ray tube and the X-ray detector;
    a control part configured to collect the projection data from plural angular directions obtained through rotation of the X-ray tube and the X-ray detector by the rotating part, performs reconstruction computation of these collected projection data to produce tomographic images of the object as well as controls the X-ray tube and the rotating part;

a display part configured to display the produced tomographic images;

a projection data analysis part configured to reconstruct a tomographic image at an imaging portion of the object used for analysis from the projection data, and produce a control profile by reprojecting the reconstructed tomographic image during real scanning, and a tube current control part configured to modify or renew, during said real scanning and based on the control profile produced by the projection data analysis part, a value of current to be fed back to the X-ray tube.

* * * * *